US00PP16049P2

(12) United States Plant Patent
Geers

(10) Patent No.: US PP16,049 P2
(45) Date of Patent: Oct. 18, 2005

(54) ***TAXUS* PLANT NAMED 'GEERS'**

(50) Latin Name: *Taxus×media*
Varietal Denomination: Geers

(75) Inventor: Peter Geers, Boskoop (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 2 days.

(21) Appl. No.: 10/878,605

(22) Filed: Jun. 28, 2004

(51) Int. Cl.[7] ..... A01H 7/00
(52) U.S. Cl. ..... Plt./215
(58) Field of Search ..... Plt./215

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Taxus* plant named 'Geers', characterized by its outwardly spreading and arching plant form; bright yellow green-colored leaves; foliage resistant to sun and winter burning; and tolerance to low temperatures.

1 Drawing Sheet

Botanical classification/cultivar designation: *Taxus×media* cultivar Geers.

BACKGROUND OF THE INVENTION

The present Invention relates to a new and distinct cultivar of *Taxus,* botanically known as *Taxus×media*, and hereinafter referred to by the name 'Geers'.

The new *Taxus* is a naturally-occurring branch mutation of the *Taxus×media* cultivar Hicksii, not patented. The Inventor discovered the new *Taxus* as a single branch mutation within a population of plants of the parent 'Hicksii' in a controlled environment in Boskoop, The Netherlands in 1986.

Asexual reproduction of the new *Taxus* by hardwood cuttings in a controlled environment in Boskoop, The Netherlands since 1996 has shown that the unique features of this new *Taxus* are stable and reproduced true to type in successive generations.

SUMMARY OF THE INVENTION

Plants of the cultivar Geers have not been observed under all possible environmental conditions. The phenotype may vary somewhat with variations in environment and culture such as temperature and light intensity without, however, any variance in genotype.

The following traits have been repeatedly observed and are determined to be the unique characteristics of 'Geers'. These characteristics in combination distinguish 'Geers' as a new and distinct cultivar of *Taxus:*

1. Outwardly spreading and arching plant form.
2. Bright yellow green-colored leaves.
3. Foliage resistant to sun and winter burning.
4. Tolerant to low temperatures.

Plants of the new *Taxus* are most similar to plants of the parent, the cultivar Hicksii. Plants of the new *Taxus* differ primarily from plants of the cultivar Hicksii in the following characteristics:

1. Plants of the new *Taxus* are slower growing than plants of the cultivar Hicksii.

2. Plants of the new *Taxus* are shorter, but more outwardly spreading and not as upright as plants of the cultivar Hicksii.
3. Plants of the new *Taxus* are more freely branching than plants of the cultivar Hicksii.
4. Plants of the new *Taxus* and the cultivar Hicksii differ in foliage coloration as plants of the cultivar Hicksii have dark green-colored foliage.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Taxus.*

The photographs on the sheet comprise side perspective views of a typical plant of 'Geers' grown in the landscape.

DETAILED BOTANICAL DESCRIPTION

Plants used for the aforementioned photographs and following observations and measurements were grown in Grand Haven, Mich., during the summer in an outdoor nursery and under conditions which approximate commercial *Taxus* production. During the winter plants were grown in a polyethylene-covered greenhouse. Plants had been growing for about two years when the photographs and description were taken.

In the following description, color references are made to The Royal Horticultural Society Colour Chart, 1995 Edition, except where general terms of ordinary dictionary significance are used.

Botanical classification: *Taxus×media* cultivar Geers.
Parentage: Naturally-occurring branch mutation of the *Taxus×media* Hicksii, not patented.
Propagation:
*Type.*—By hardwood cuttings.
*Time to initiate roots.*—About one month at 10° C.

*Time to produce a rooted cutting*.—About three months at 10° C.

*Root description*.—Thick, fibrous; white in color.

*Rooting habit*.—Freely branching; dense.

Plant description:

*Form*.—Outwardly spreading and arching perennial evergreen tree.

*Branching habit*.—Freely branching with branches outwardly arching, branchlets borne in the same plane; about 112 branches per plant. Trees maintain their lower branches and foliage to the soil level.

*Plant height*.—About 43 cm.

*Plant diameter*.—About 35 cm.

*Branch description*.—Length: About 29 cm. Diameter: About 3.5 mm. Internode length: About 4 mm. Color: 143A.

*Bark description*.—Woody, 177B.

*Winter bud description*.—Length: About 4 mm. Width: 2 mm. Shape: Acute with imbricate scales. Color: 166B.

*Leaf description*.—Arrangement: Alternate, simple. Length: About 2 cm. Width: About 3 mm. Shape: Linear, flattened. Apex: Acute. Base: Cuneate. Margin: Entire. Venation pattern: Linear. Color: Foliage resistant to sun and winter burning. Developing and fully expanded leaves, upper surface: 144C. Developing and fully expanded leaves, lower surface: 144B; stomata bands not observed. Venation, upper and lower surfaces: Same as lamina. Petiole length: About 1.5 mm. Petiole diameter: About 0.5 mm. Petiole color, upper and lower surfaces: 144B.

Cone description: Cone development has not been observed.

Disease/pest resistance: Plants of the new *Taxus* have not been noted to be resistant to pathogens or pests common to *Taxus*.

Weather tolerance: Plants of the new *Taxus* have been observed to be tolerant to drought, rain, wind and temperatures ranging from −25 to 30° C.

It is claimed:

1. A new and distinct cultivar of *Taxus* plant named 'Geers', as illustrated and described.

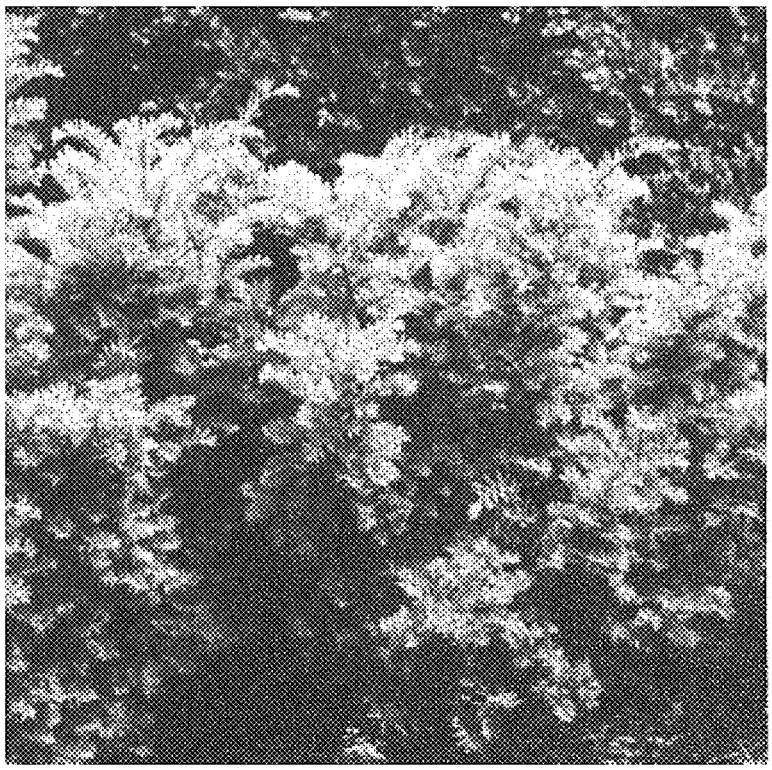
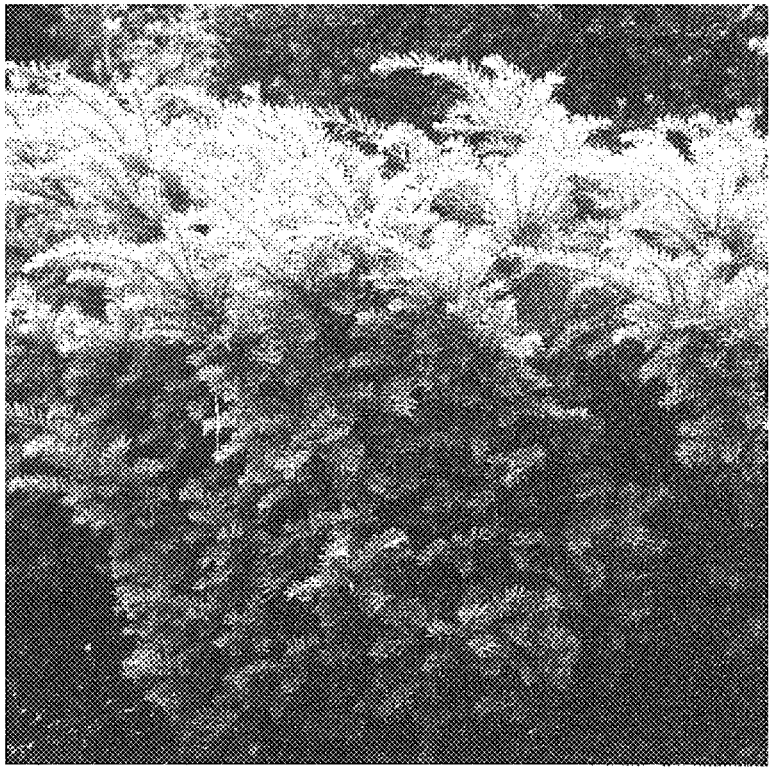

* * * * *